(12) United States Patent
Oskam

(10) Patent No.: US 10,052,182 B2
(45) Date of Patent: Aug. 21, 2018

(54) METHOD FOR GENERATING A MODEL OF A DENTAL REPLACEMENT PART

(71) Applicant: SIRONA DENTAL SYSTEMS GMBH, Bensheim (DE)

(72) Inventor: Thomas Oskam, Schaffhausen (CH)

(73) Assignee: DENTSPLY SIRONA Inc., York, PA (US)

( * ) Notice: Subject to any disclaimer, the term of this patent is extended or adjusted under 35 U.S.C. 154(b) by 0 days.

(21) Appl. No.: 15/522,787

(22) PCT Filed: Oct. 29, 2015

(86) PCT No.: PCT/EP2015/075090
§ 371 (c)(1),
(2) Date: Apr. 28, 2017

(87) PCT Pub. No.: WO2016/066736
PCT Pub. Date: May 6, 2016

(65) Prior Publication Data
US 2017/0333164 A1 Nov. 23, 2017

(30) Foreign Application Priority Data
Oct. 29, 2014 (DE) .......... 10 2014 222 037

(51) Int. Cl.
*A61C 13/00* (2006.01)
*A61C 13/08* (2006.01)

(52) U.S. Cl.
CPC .......... *A61C 13/0004* (2013.01); *A61C 13/08* (2013.01)

(58) Field of Classification Search
None
See application file for complete search history.

(56) References Cited

U.S. PATENT DOCUMENTS

| | | |
|---|---|---|
| 8,359,114 B2 | 1/2013 | Steingart et al. |
| 2008/0124679 A1 | 5/2008 | Orth et al. |
| 2009/0246726 A1 | 10/2009 | Chelnokov et al. |
| 2010/0167243 A1 | 7/2010 | Spiridonov et al. |
| 2011/0038514 A1 | 2/2011 | Weigl |

(Continued)

FOREIGN PATENT DOCUMENTS

| | | |
|---|---|---|
| GB | 359195 A | 10/1931 |
| WO | 2013124260 A2 | 8/2013 |

*Primary Examiner* — Whitney T Moore
(74) *Attorney, Agent, or Firm* — Dentsply Sirona Inc.

(57) ABSTRACT

The invention relates to a method for generating a digital model (6) of a dental replacement part, formed by a dental prosthesis and a prosthesis base having a rear protection plate, and for producing a dental replacement part of this type, wherein, in a digital model (1) of a jawbone to be provided and a digital dental prosthesis model (2) positioned therein, an interface (3) is automatically and/or manually marked in the region of the dental prosthesis model (2), a rear protection plate model (4) is formed by the interface (3), an abutting surface (1') of the digital jawbone model (1) and a region of a surface (2') of the dental prosthesis model (2) joining the surface (1') and the interface (3), a revised dental prosthesis model (5) is formed from the digital dental prosthesis model (2) by adopting the interface (3) as a surface, and the digital model (6) of the dental replacement part is created from the rear protection plate model (4) and the revised dental prosthesis model (5).

16 Claims, 1 Drawing Sheet

(56) References Cited

U.S. PATENT DOCUMENTS

2013/0158694 A1* 6/2013 Rubbert .............. A61C 8/0018
700/98
2013/0316302 A1 11/2013 Fisker
2014/0051037 A1 2/2014 Fisker
2017/0333164 A1 11/2017 Oskam

* cited by examiner

METHOD FOR GENERATING A MODEL OF A DENTAL REPLACEMENT PART

TECHNICAL FIELD

The invention relates to a method for generating a digital model of a dental replacement part consisting of a dental prosthesis and a prosthesis base, wherein the prosthesis base comprises at least one rear protection plate. The invention further relates to a method for producing such a dental replacement part.

BACKGROUND OF THE INVENTION

Nowadays, dental replacement parts are mostly designed and produced with the aid of digital means.

For example, WO 2012/041329 A1 and WO 2012/083959 A1 describe methods that produce a digital model for the production of a dental replacement part consisting of a dental prosthesis and a prosthesis base. For this purpose, a three-dimensional digital representation of the jawbone to be provided is, in particular, used.

In U.S. Pat. No. 8,359,114 B2, a dental restoration is designed by means of a haptic interface.

Some dental replacement parts, such as model cast prostheses, require additional, reinforcing structures, such as retaining and supporting elements. For example, it is customary to reinforce the model cast prosthesis by a rear protection plate when replacing one or more front teeth by a model cast prosthesis. It is problematic to integrate the rear protection plate into the dental replacement part such that, on the one hand, a sufficient stability can be ensured and, on the other, it is ensured that the artificial teeth feel natural in the mouth of the patient and are positioned as desired.

The aim of the present invention is now to provide a method for generating a digital model of a dental replacement part comprising such a rear protection plate, as well as a method for its production, which ensures high stability, as well as great precision, with respect to position and fitting accuracy.

SUMMARY OF THE INVENTION

The object of the invention is a method for generating a digital model of a dental replacement part consisting of a dental prosthesis and a prosthesis base comprising-a rear protection plate. The method provides that, in a digital model of a jawbone or a jawbone section to be provided, and of a digital dental prosthesis model positioned therein, an interface is automatically and/or manually marked in the region of the dental prosthesis model. A rear protection plate is formed by the interface, an abutting surface of the digital model, and a region of a surface of the dental prosthesis model joining the abutting surface of the jawbone model and the interface. Furthermore, a revised dental prosthesis model is formed from the digital dental prosthesis model by adopting the interface as a surface. The digital model of the dental replacement part is then produced from the rear protection plate model and the revised dental prosthesis model.

The invention relates to an arbitrary dental replacement part, which is composed of a dental prosthesis, which can also be called an artificial tooth, and a retaining device referred to as prosthesis base, wherein the prosthesis base comprises a rear protection plate.

A rear protection plate is a structure reinforcing the dental prosthesis, which structure at least partially protrudes into the dental prosthesis for this purpose. Such a rear protection plate is, for example, necessary or is, for example, used, when one or more front teeth are replaced by a prosthesis.

In order to achieve a high wearing comfort, a rear protection plate must preferably recreate the surface of the dental prosthesis. Furthermore, it must be ensured that the dental prosthesis attached to the rear protection plate is located precisely at the desired position after inserting the entire dental replacement part into a jawbone to be provided. In order to be able to ensure a desired stability, the rear protection plate must furthermore have a sufficient thickness, i.e., it must protrude into the dental prosthesis to a sufficient extent. The stability can further be improved by a reinforcement of the rear protection plate in the direction of abutting elements, such as in the direction of the jawbone.

The starting point of the method is a digital model of the jawbone or jawbone section to be provided, with a digital dental prosthesis model positioned therein. The digital model of the jawbone, also called a jawbone model, can, for example, be produced using a three-dimensional measurement of the jawbone to be provided, i.e., an intra-oral measurement, or by measuring a physical model of the jawbone, such as a jawbone plaster model.

The digital dental prosthesis model can, for example, be produced by the three-dimensional measurement of a physical dental prosthesis model placed on a physical jawbone model. For example, a dental prosthesis model can be positioned on the jawbone plaster model using wax (Wax-Up), and scanned. The two data sets of the jawbone plaster model, with and without a dental prosthesis positioned thereon, can then be correlated based upon the corresponding regions, and the digital model of the jawbone according to the invention can thus be produced with the positioned, digital dental prosthesis model.

It is also possible to digitally produce a virtual dental prosthesis model and to position it in a digital model of the jawbone to be provided, in order to obtain the digital model according to the invention with the positioned dental prosthesis.

The marking of the interface, which is to serve as interface between the rear protection plate and the dental prosthesis, can be carried out completely by a user, fully automatically, or by a combination of user inputs and automated steps.

The method ensures that the rear protection plate has an oral surface which exactly corresponds to the desired oral surface of the dental prosthesis, and that the dental prosthesis comes to stand precisely at the desired position after being attached to the rear protection plate and inserted into the jawbone. In particular, by automated steps in the production of the interface, undercuts or the protrusion of the rear protection plate into the jawbone can be reliably prevented. Pre-determined breaking points can also be avoided, or an optimal shape of the rear protection plate with respect to stability can be achieved.

Advantageously, the interface is produced by moving a starting surface, marked automatically and/or manually on an oral surface of the dental prosthesis model and/or the digital model of the jawbone, by a specified depth in a substantially vestibular direction.

This can ensure that the rear protection plate to be produced or the digital rear protection plate model has a sufficient thickness over its entire height, in order to ensure the desired stability. A typical thickness is, for example, about 0.6 mm. Furthermore, a geometry as simple as possible of the rear protection plate or the interface can thereby be ensured.

Advantageously, the starting surface is marked by marking a circumferential line, which constitutes a particularly easy variant for producing the starting surface, with respect to both the implementation and the application.

Advantageously, the moving of the starting surface takes place along a direction which takes into consideration a direction of insertion for the dental replacement part. Undercuts can thereby be reliably avoided.

Advantageously, the interface is changed manually and/or automatically after it is marked. In this way, a user can address individual circumstances in a better way, or additional standardized properties of rear protection plates can be implemented, such as a reinforcement in the direction of the abutting jawbone or the provision of retaining elements between the rear protection plate and the dental prosthesis.

Advantageously, the interface is automatically and/or manually reinforced in a region abutting the surface of the digital model of the jawbone. The stability can be significantly increased thereby.

Advantageously, a retaining element overlapping the interface is marked automatically or manually. Traditional retaining elements, such as retaining plates, can thereby be easily provided between the rear protection plate and the dental prosthesis or integrated into the model of the dental replacement part.

Advantageously, a shape of the overlapping element is integrated into the rear protection plate model and/or the revised dental prosthesis model. The shape of the rear protection plate model or the revised dental prosthesis model can easily be adapted to overlapping elements, such as retaining plates or the like, by adopting or providing recesses or protrusions corresponding to the shape of the overlapping elements.

Advantageously, one or more corners of the interface are rounded automatically, whereby the stability can be significantly increased. Transitions between different materials, such as between the rear protection plate and the dental prosthesis, are, in particular, advantageously designed to be rounded, e.g., as a fillet, in order to avoid pre-determined breaking points.

Advantageously, a recess and/or protrusion is integrated manually and/or automatically into the interface as a connecting element. A connecting element designed as a recess or a protrusion can increase the stability of the dental replacement part. The connecting element can, for example, be integrated automatically into the interface by marking and moving a region of the interface by means of a suitable input device, such as a mouse, or even according to suitable specifications with respect to the height, position, and/or orientation of the connecting element. The connecting element can, for example, be designed as a recess of the rear protection plate in the oral direction and a corresponding protrusion of the dental prosthesis in the oral direction. The recess or protrusion can also be designed to extend diagonally upward with respect to the interface, in the manner of a watch glass holder.

The invention further relates to a method for producing a dental replacement part consisting of a dental prosthesis and a prosthesis base comprising a rear protection plate, wherein the dental replacement part is produced on the basis of a digital model of the dental replacement part generated as described above.

On the basis of the dental replacement model according to the invention, a high-quality dental replacement satisfying the aforementioned requirements can be reliably produced. The prosthesis base can be produced on the basis of the digital model generated on the basis of the rear protection plate model. The dental prosthesis can be produced on the basis of the revised dental prosthesis model. If a dental prosthesis is already available, which, for example, has served as the basis for the digital dental prosthesis model, it can be adapted to the revised dental prosthesis model.

Advantageously, a template is produced on the basis of the revised dental prosthesis model, which template has a recess, the shape of which corresponds to a negative form of the surface, extending to the interface, of the revised dental prosthesis model.

The template constitutes a simple way of grinding in an existing dental prosthesis so as to fit. If this dental prosthesis has, in particular, served as the basis for the digital dental prosthesis model, the template according to the invention can ensure a precisely-fitting grinding.

Advantageously, the template is designed to have several parts. In this way, the attachment of the template to or around the dental prosthesis to be ground can be made easier, or even made possible in the first place. Different template parts can, for example, be connected to one another using a plain key mechanism of positively interlocking elements, so that the assembly is unambiguous. The prosthesis tooth or the prosthesis teeth are surrounded by the template such that the edge region, which is to abut against the rear protection plate, is guided precisely by the template edge. The user can thus precisely grind the prosthesis tooth at the edge region, in order to subsequently be able to attach the prosthesis tooth to the rear protection plate.

BRIEF DESCRIPTION OF THE DRAWINGS

Exemplary embodiments of the invention are depicted in the drawings. In the drawings.

DETAILED DESCRIPTION OF THE INVENTION

Figure 1:
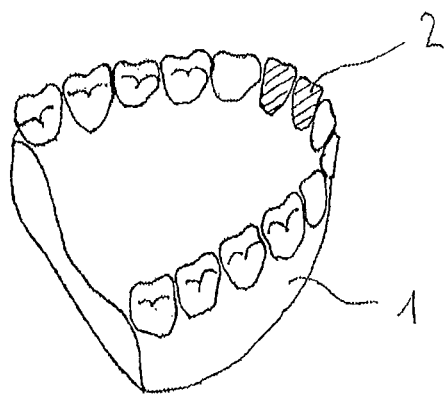
FIG. 1 shows a digital model of a jawbone to be provided with a digital dental prosthesis model positioned therein.

FIG. 1 shows a digital model 1 of a jawbone to be provided, which model can, for example, be produced by means of a scan using an intra-oral camera. In the digital model 1, a digital dental prosthesis model 2, which is illustrated in a shaded manner for better identifiability, is positioned at flaws of the jawbone to be provided.

Figure 2:
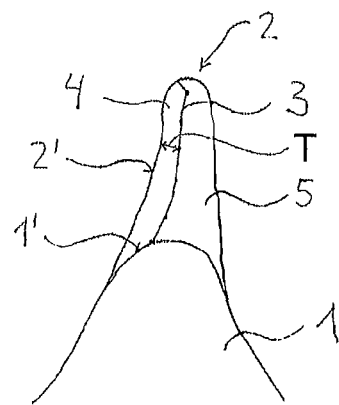
FIG. 2 shows a cross-sectional profile of the model according to FIG. 1 in the region of the positioned digital dental prosthesis model.

FIG. 2 shows a cross-sectional profile of the digital model 1 depicted in FIG. 1 in the region of the dental prosthesis model 2. According to the method according to the invention, an interface 3, which can be seen in the cross-sectional profile of FIG. 2 as a profile, is marked in the dental prosthesis model 2. The interface 3 extends from a surface 2' of the dental prosthesis model 2 to a surface 1' of the digital model 1 of the jawbone. This interface 3 serves as interface between a rear protection plate model 4 to be produced and a revised dental prosthesis model 5, which serve as the basis for a dental replacement part model 6 (not shown in FIG. 5) to be produced.

The rear protection plate model 4 is formed by the interface 3, an abutting section of the surface 1' of the digital model 1 of the jawbone, and a section of the surface 2' of the dental prosthesis model 2, which section extends orally between the surface 1' of the digital jawbone model 1 and the interface 3.

The revised dental prosthesis model 5 is formed by the digital dental prosthesis model 2 and the interface 3 so that the section, occupied by the rear protection plate model 4, of the dental prosthesis model is cut off or removed, so to speak, by the interface 3.

Figure 3:
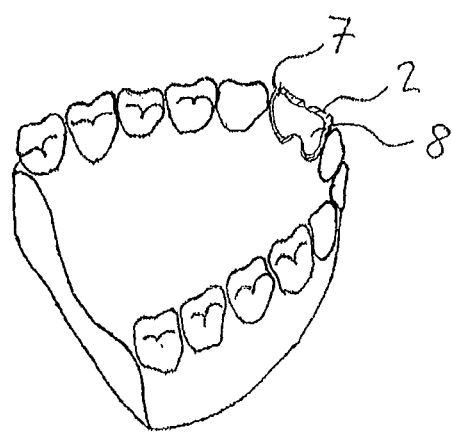
FIG. 3 shows a marking of a starting surface in a model according to FIG. 1.

The interface 3 can be marked manually, e.g., by means of an input device, such as a mouse. This can, for example, be carried out by a marking of the entire surface or even by a marking of a line delimiting the surface. An automatic marking of the interface 3 is also possible. For this purpose, a starting surface 8 can, for example, be automatically estimated or manually marked on an oral surface 7 of the dental prosthesis model 2 (FIG. 3). The interface 3 is then produced in the dental prosthesis model 2 by a substantially parallel movement of the starting surface 8 in the vestibular direction.

A depth T is specified as the distance of the movement (FIG. 2). This corresponds, for example, to a typical thickness of a rear protection plate of 0.6 mm, for example. For the automatic movement, the starting surface 8 is, for example, parameterized, wherein a previously defined insertion axis of the dental replacement part to be produced is advantageously taken into account with respect to the parameterization and with respect to the direction of the movement.

The interface 3 produced in this way can still subsequently be changed, or optimized manually and/or automatically. In order to increase the stability, an overlapping retaining element is generally provided between the dental prosthesis and the rear protection plate, for example. This retaining element can first be marked and positioned in the profile of the digital model 1, e.g., in the manner illustrated in FIG. 4, as overlapping element 9, i.e., as an element protruding beyond the interface 3 on both sides. Subsequently, the shape of the overlapping element 9 is adopted in the digital model 6 to be generated of the dental replacement part such that the shape of the overlapping element 9 is completely adopted in the shape of one of the two abutting components or models 4, 5 for the rear protection plate or the dental prosthesis, and the other component or model 4, 5 has a corresponding recess.

Figure 4:
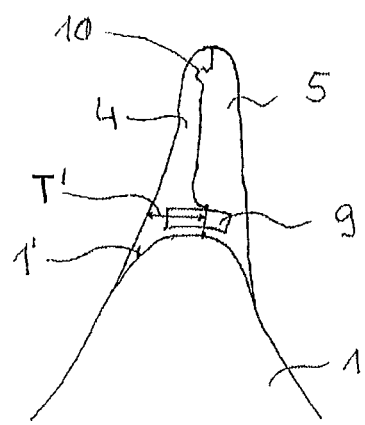
FIG. 4 shows the cross-sectional profile from FIG. 2 with a changed interface and an overlapping element.

Another variant for increasing the stability is to manually and/or automatically move the interface 3 a little further in the vestibular direction in a region abutting the surface 1' of the jawbone model 1, so that the rear protection plate model 4 to be produced is reinforced in a region abutting the digital model 1 of the jawbone (FIG. 4). If the model 6 to be produced of a dental replacement part is designed with an overlapping element 9, it is particularly advantageous if such a reinforcement ends with the overlapping element 9, such that the rear protection plate model 4 has, at least in a region of the overlapping element 9 and in a region located between the overlapping element 9 and the surface 1' of the jawbone model 1, a depth T' that is greater than the specified depth T.

The rounding of the corners, furthermore, adds to the increase in stability, so that the corners are, for example, designed as fillets. For this purpose, a rounding of the corners of the interface 3 is carried out manually and/or automatically, as can be seen by way of example in FIG. 4 in the profile of the interface 3 above the overlapping element 9. In particular, in an embodiment of the dental replacement part with an overlapping element 9, such as a retaining plate, the rounding of the abutting corner of the interface 3 is advantageous, since, especially, transitions of different materials are preferably to be designed in the manner of fillets or watch glass holders.

Another possibility for increasing the stability of the dental replacement part to be produced is the provision of at least one connecting element 10. An exemplary embodiment of such a connecting element 10 can also be seen in FIG. 4. The connecting element 10 consists of a recess on the part of the rear protection plate model 4 and a protrusion on the part of the revised dental prosthesis model, wherein the recess, as well as the protrusion, extend diagonally in an incisal or occlusal direction with respect to the interface 3, in the manner of a watch glass holder.

Figure 5:
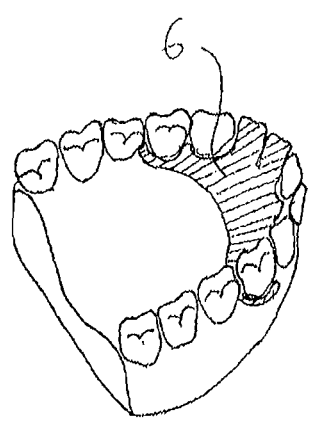
FIG. 5 shows a model, produced according to the invention, of a dental replacement part.

After a final determination of the interface 3, the rear protection plate model 4 and the revised dental prosthesis model 5 are, as already described, generated on the basis of this interface 3, the digital jawbone model 1, and/or the dental prosthesis model 2, and, if applicable, the overlapping element 9, and assembled and/or complemented to produce a dental replacement part model 6, as sketched in FIG. 5 in a shaded manner. The rear protection plate model 4 can, for example, be complemented by known method steps so as to produce a dental prosthesis base model for a dental prosthesis base with retaining devices for attaching the dental prosthesis to neighboring teeth.

The produced dental replacement part model 6 can, furthermore, be used to produce a dental replacement part consisting of a dental prosthesis base with a rear protection plate and a dental prosthesis. For this purpose, the dental prosthesis and the dental prosthesis base can be produced according to the respective model data, e.g., by casting processes or milling processes from appropriate, conventional materials, such as ceramic or metal.

Figure 6:
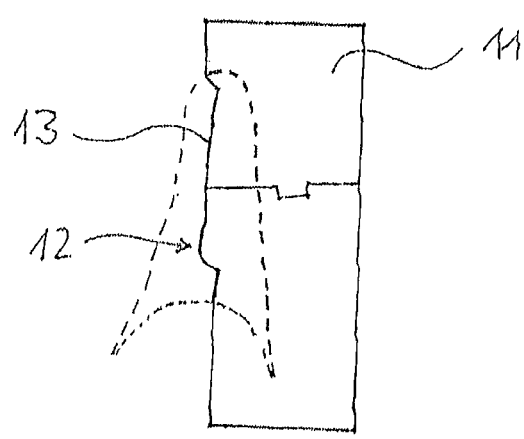
FIG. 6 shows a template according to the invention.

If a dental prosthesis is already available and was, for example, the basis for the dental prosthesis model 2, it is particularly advantageous to produce, on the basis of the revised dental prosthesis model 4, a template 11, with which the dental prosthesis can be adapted to the revised dental prosthesis model 5. As shown in FIG. 6, the template 11 can, advantageously, have several parts. The individual parts of the template 11 can, advantageously, be connected to one another using unambiguously interconnecting keys, in order to avoid errors as a result of incorrect assembly.

The template 11 comprises a recess 12, the shape of which corresponds to a negative form of the revised dental prosthesis model 5, wherein an edge 13 of the recess 12 precisely corresponds to an edge of the interface 3. In this way, the already existing dental prosthesis (in this case, illustrated with dashes) can be inserted into the recess, and the protruding region can be removed, for example, by grinding.

LIST OF REFERENCE SYMBOLS

1 Digital model of a jawbone to be provided
1' Surface of the digital jawbone model 1
2 Digital dental prosthesis model
2' Surface of the dental prosthesis model 2
3 Interface
4 Rear protection plate model
5 Revised dental prosthesis model
6 Dental replacement part model
7 Oral surface of the dental prosthesis model 2
8 Starting surface
9 Overlapping element 10 Connecting element
11 Template
12 Recess
13 Edge
T Depth
T' Depth

The invention claimed is:

1. Method for generating a digital model of a dental replacement part including a dental prosthesis and a prosthesis base having a rear protection plate, the method comprising the steps of: -providing a digital model of a jawbone or a jawbone section having a digital dental prosthesis model positioned therein, wherein an interface is automatically and/or manually marked in a region of the dental prosthesis model, -forming a rear protection plate model by the interface, an abutting surface of the digital jawbone model, and a region of a surface of the dental prosthesis model joining the surface of the digital jawbone model and the interface, -forming a revised dental prosthesis model from the digital dental prosthesis model by adopting the interface as a surface, and -producing the dental replacement part based on the digital model, -wherein the interface is produced by moving a starting surface, marked automatically and/or manually on an oral surface of the dental prosthesis model and/or of the digital jawbone model, by a specified depth (T) in a substantially vestibular direction.

2. Method according to claim 1, wherein the starting surface is marked by marking a circumferential line.

3. Method according to claim 1, wherein the movement of the starting surface occurs along a direction which takes into consideration a direction of insertion for the dental replacement part.

4. Method according to claim 1 wherein the interface is changed manually and/or automatically after being marked.

5. Method according to claim 1, wherein the interface is automatically and/or manually reinforced in a region abutting the surface of the digital model of the jawbone or jawbone section.

6. Method according to claim 1, wherein an element overlapping the interface is marked automatically or manually.

7. Method according to claim 6, wherein the overlapping element is integrated into the rear protection plate model and/or the revised dental prosthesis model.

8. Method according to claim 6, further comprising reinforcing the rear protection plate model in a region abutting the digital model of the jawbone or the jawbone section such that the reinforcement ends with the overlapping element, wherein the rear protection plate model has, at least in a region of the overlapping element and in a region located between the overlapping element and the abutting surface of the digital model of the jawbone or the jawbone section, a depth T' that is greater than the specified depth T.

9. Method according to claim 1, wherein one or more corners of the interface are automatically rounded.

10. Method according to claim 1, wherein a recess or protrusion is manually and/or automatically integrated into the interface as a connecting element.

11. Method according to claim 10, further comprising designing the recess or protrusion to extend diagonally upward with respect to the interface.

12. Method for producing a dental replacement part having a dental prosthesis and a prosthesis base having a rear protection plate, the method comprising the steps of producing the dental replacement part on the basis of a digital model, generated according to claim 1, of the dental replacement part.

13. Method for producing a dental replacement part according to claim 12, wherein a template is produced on the basis of the revised dental prosthesis model, which template has a recess, the shape of which corresponds to a negative form of a vestibular surface, extending to the interface, of the revised dental prosthesis model.

14. Method for producing a dental replacement part according to claim 13, wherein the template is designed to have several parts.

15. Method according to claim 1, wherein the specified depth (T) corresponds to a thickness of the rear protection plate.

16. Method according to claim 15, wherein the specified depth (T) is 0.6 mm.

* * * * *